(12) United States Patent
Armbruster et al.

(10) Patent No.: US 11,085,922 B2
(45) Date of Patent: Aug. 10, 2021

(54) METHOD OF MEASURING AUTO-ANTIBODIES IN BODILY FLUIDS

(71) Applicant: Immundiagnostik AG, Bensheim (DE)

(72) Inventors: Franz Paul Armbruster, Bobenheim-Roxheim (DE); Moritz Leppkes, Nuremberg (DE)

(73) Assignee: Immundiagnostik AG, Bensheim (DE)

( * ) Notice: Subject to any disclaimer, the term of this patent is extended or adjusted under 35 U.S.C. 154(b) by 33 days.

(21) Appl. No.: 16/219,903

(22) Filed: Dec. 13, 2018

(65) Prior Publication Data
US 2019/0204311 A1   Jul. 4, 2019

(30) Foreign Application Priority Data

Dec. 13, 2017 (DE) .................... 10 2017 129 738.3
Mar. 20, 2018 (EP) .................... 18162895

(51) Int. Cl.
*G01N 33/543* (2006.01)
*G01N 33/564* (2006.01)
*G01N 33/68* (2006.01)

(52) U.S. Cl.
CPC ..... *G01N 33/54313* (2013.01); *G01N 33/564* (2013.01); *G01N 33/6854* (2013.01)

(58) Field of Classification Search
None
See application file for complete search history.

(56) References Cited

U.S. PATENT DOCUMENTS

| | | | |
|---|---|---|---|
| 6,159,748 A * | 12/2000 | Hechinger | C12Q 1/6816 435/5 |
| 6,787,660 B1 | 9/2004 | Armbruster et al. | |
| 7,851,163 B2 | 12/2010 | Armbruster et al. | |
| 7,943,579 B2 | 5/2011 | Armbruster | |
| 7,964,363 B2 | 6/2011 | Armbruster et al. | |
| 8,133,694 B2 | 3/2012 | Armbruster et al. | |
| 9,140,711 B2 | 9/2015 | Armbruster et al. | |
| 9,823,258 B2 | 11/2017 | Armbruster et al. | |
| 2007/0087395 A1 | 4/2007 | Armbruster et al. | |
| 2011/0003311 A1 | 1/2011 | Armbruster et al. | |
| 2015/0017738 A1 | 1/2015 | Armbruster et al. | |
| 2016/0025748 A1 | 1/2016 | Armbruster et al. | |
| 2019/0234936 A1* | 8/2019 | Fuchs | G01N 33/5005 |

FOREIGN PATENT DOCUMENTS

| | | |
|---|---|---|
| EP | 3273238 A1 | 1/2018 |
| WO | 2016/138899 A1 | 9/2016 |

OTHER PUBLICATIONS

Specks et al., Efficacy of Remission-Induction Regimens for ANCA-Associated Vasculitis, N Engl. J. Med. Aug. 1, 2013; 369(5); 417-427. (Year: 2013).*
Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, ,pp. 1-7. (Year: 2014).*
Dwivedi et al., Felty's Syndrome Autoantbodies Bind to Deiminated Histones and Neutrophil Extracellular Chromatin Traps, Arthritis and Rheumatism vol. 64, No. 4, Apr. 2012, pp. 982-992. (Year: 2012).*
Schulte-Pelkum et al., "Novel Clinical and Diagnostic Aspects of Antineutrophil Cytoplasmic Antibodies," J. Immunol. Res., 2014, 1-12 (2014).
Hsieh et al., "Anti-myeloperoxidase Antibodies Enhance Phagocytosis, IL-8 Production, and Glucose Uptake of Polymorphonuclear Neutrophils Rather Than Anti-proteinease 3 Antibodies Leading to Activation-induced Cell Death of the Neutrophils," Clin. Rheumatol., 26, 216-224 (2006).
Sangaletti et al., "Neutrophil Extracellular Traps Mediate Transfer of Cytoplasmic Neutrophil Antigens to Myeloid Dendritic Cells Toward ANCA Induction and Associated Autoimmunity," Blood, 120, 3007-3018 (2012).

* cited by examiner

*Primary Examiner* — Gary Counts
(74) *Attorney, Agent, or Firm* — James C. Lydon

(57) ABSTRACT

A method for detecting and quantifying anti-neutrophil-cytoplasmic antibodies (ANCA) in a sample of bodily fluid from a patient suspected of suffering from an autoimmune disease, including the steps of contacting human polymorphonuclear neutrophils able to release extracellular traps (NETs) with microspheres to produce NET-coated microspheres, contacting the NET-coated microspheres with the sample of bodily fluid, and labeling and subsequent analyzing of anti-neutrophil-cytoplasmic antibodies by flow cytometric methods.

7 Claims, 5 Drawing Sheets antibody-based detection
of NET-bound antigens

— Uncoated microbeads (Staining control)
— — Uncoated microbeads (Specific staining)
----- NET-coated microbeads (Specific staining)

METHOD OF MEASURING AUTO-ANTIBODIES IN BODILY FLUIDS

CROSS-REFERENCE TO RELATED APPLICATIONS

The instant invention claims priority to earlier German Patent Application No. 10 2017 129 738.3 filed Dec. 13, 2017 and European Patent Application No. 18162895.9 filed 20 Mar. 2018, the teaching of which are hereby incorporated by reference in their entirety.

FIELD OF THE INVENTION

The present invention relates to a kit of parts, means, and methods for detection and characterization of autoantibodies in a sample of a patient suspected of suffering from an autoimmune disease.

BACKGROUND OF THE INVENTION

An autoimmune disease is a condition arising from an immune response against endogenous components of the organism. Representative common autoimmune diseases include celiac disease, diabetes mellitus type 1, inflammatory bowel disease, multiple sclerosis, psoriasis, rheumatoid arthritis, and systemic lupus erythematosus. Their etiologies are poorly understood.

Vasculitis is a group of disorders, some of them autoimmune diseases, that destroy blood vessels by inflammation. Both arteries and veins are affected. Vasculitis is primarily caused by leukocyte migration and resultant damage. Vasculitis can be classified by the cause, the location, the type of vessel or the size of vessel. There is usually an immune component, but the trigger is often not identified. The antibody found is sometimes used in classification, as in ANCA-associated vasculitides. ANCA are anti-neutrophil cytoplasmic auto-antibodies which recognize polymorphonuclear neutrophil granulocytes (PMN) and arise during chronic inflammation (Savige et al, 2003 "*Addendum to the International Consensus Statement on Testing and Reporting of Antineutrophil Cytoplasmic Antibodies*" American Journal of Clinical pathology/120 (3) 312-318). Granulomatosis with polyangiitis (GPA), microscopic polyangiitis (MPA) and eosinophilic granulomatosis with polyangiitis (EGPA) are representative examples of ANCA-associated vasculitides (AAV). They are accompanied with an inflammation of small-to-medium-sized blood vessels, and a long-term immunosuppressive therapy is required to maintain sufficient kidney function (Jennette et al, 2013 "*2012 revised International Chapel Hill Consensus Conference Nomenclature of Vasculitides*", Arthritis and rheumatism 66 (1) 1-11). The detection and measurement of ANCA in bodily fluids has therefore become a diagnostic tool not only in the classification of autoimmune diseases but also for assessing, predicting and/or monitoring disease occurrence and relapse (Lionaki et al, 2012 "*Classification of anti-neutrophil cytoplasmic autoantibody vasculitides: the role of antineutrophil cytoplasmic autoantibody specificity for myeloperoxidase or proteinase 3 in disease recognition and prognosis*", Arthritis and rheumatism 64 (10) 3452-3462).

Most clinical laboratories screen and detect anti-neutrophil cytoplasmic antibodies (ANCA) by indirect immunofluorescence (IIF), say by a detection of ANCA on cytoplasmic antigens from human neutrophil granulocytes. Proteinase 3 (PR3), myeloperoxidase (MPO), elastase, cathepsin G, lysozyme, lactoferrin, or bactericidal permeability increasing protein (BPI) are antigens that are typically bound by ANCA in serum or plasma. Anti-PR3 and anti-MPO have therefore become serologic markers for ANCA-associated vasculitides in clinical chemistry (Savige et al, 2003; Schönermarck U et al, 2015 "*Pathogenesis of anti-neutrophil cytoplasmic antibody-associated vasculitis: challenges and solutions*", Nephrol Dial Transplant. 30, issue suppl. 1, April 2015, i46-i52). However, the serological patterns differ among the ANCA-associated vasculitides in antigen specificity and the presence of complex antigens like DNA-protein complexes (Tesija Juna 2013 "*Serological markers of inflammatory bowel disease*", Biochem Med. 28-42; Zhou et al. 2016 "*ASCA, ANCA, ALCA and Many More; Are They Useful in the Diagnosis of Inflammatory Bowel Disease*? Digestive diseases (Basel, Switzerland) 34 (1-2), 90-97; Savige et al. 2003).

WO 2016/138899 A1 discloses an in vitro stimulation of polymorphonuclear neutrophil granulocytes (PMNs) for a release of chromatin and cytoplasmic antigens and subsequent immunocytochemical analysis of ANCA by microscopy. The stimulation of the neutrophil granulocytes is obtained in vitro by the addition of phorbol 12-myristate 13-acetate (PMA), also known as 12-O-tetradecanoylphorbol 13-acetate (TPA) (David A. et al, 2003 "*Interaction of proteinase 3 with CD11b/CD 18 (β2 10 integrin) on the cell membrane of human neutrophils*", Journal of Leukocyte Biology 74, 551557). Others use a calcium-ionophore for stimulation (Godfrey et al, 1987, "*Stimulus-Specific Induction of Phospholipid and Arachidonic Acid Metabolism in Human Neutrophils*" The Journal of Cell Biology 104, 925-932). In response to such stimuli, the polymorphonuclear neutrophil granulocyte (PMN) decondenses the nucleus and releases chromatin in structural forms known as neutrophil extracellular traps (NET). The NETs are decorated with or contain entangled cytoplasmic proteins and from the cell granules which can be bound by ANCA (Brinkmann and Zychlinsky 2012 "*Neutrophil extracellular traps: is immunity the second function of chromatin?*" The Journal of cell biology 198 (5) 773-783). The binding of ANCA to the granular and nuclear content of the neutrophil granulocytes can then be analyzed using immunocytochemistry. The immuncytochemistry disclosed in WO 2016/138899 A1 allows no easy quantitation of the level of the autoimmune response and no monitoring of the immunsuppressive therapy. A computerized image analysis of the indirect immunofluorescence has been proposed for monitoring of the ANCA level in serum or plasma but this method cannot be implemented as a routine laboratory method. Better detection and quantitative methods for ANCA are therefore desired. The state of the art therefore represents a problem.

SUMMARY OF THE INVENTION

The present application provides an improved method of detecting and quantifying auto-antibodies in a sample of bodily fluid from a patient suspected of suffering from ANCA-associated vasculitides, comprising the steps of (a) contacting a defined sample of serum or plasma suspected of containing human auto-antibodies under antibody-binding conditions with a defined number or amount of microspheres that have been associated or coupled with one or more ANCA-targeting antigens from polymorphonuclear neutrophils (PMN), selected from the group of cytoplasmic and granular haptens, antigens, and immunogens and their complexes with nuclear proteins, histones and nucleic acids; and (b) subjecting the sample to flow-cytometry to determine the number or fraction of microspheres having bound auto-antibodies and/or to obtain a sample of microspheres wherein the amount of bound auto-antibodies is determined.

A preferred embodiment comprises the use of labeled secondary antibodies or fragments thereof specifically recognizing human immunoglobulins (IgG, IgE, IgD, IgM, IgA). In a most preferred embodiment, the labeled second antibodies, or fragments thereof, are added to the sample of bodily fluid prior flow cytometry to obtain labeled ANCA-bound microspheres.

A most preferred embodiment comprises the use of microspheres associated or coupled with one or more ANCA target antigens. Antigens for detecting and quantification of anti-neutrophil cytoplasmic auto-antibodies in serum or plasma are proteins and DNA-protein complexes in the cytoplasms of human neutrophil granulocytes. The ANCA antigens can be associated by chromatin entanglement or adsorption or chemical coupling to uniform microspheres, e.g. polystyrene or latex beads, which may further contain a label for sorting and classification. The microspheres are preferably decorated with a whole-fraction of cytoplasmic antigens and chromatin from human polymorphonuclear neutrophils (PMN). Most preferred is the use of microspheres that have been coupled to one or more of the following antigens selected from the group comprising proteinase 3 (PR3), myeloperoxidase (MPO), elastase cathepsin G, lysozyme, lactoferrin, or bactericidal permeability increasing protein (BPI). These PMN cytoplasmic antigens typically bind auto-antibodies of ANCA-associated vasculitides.

The disclosure further encompasses a method of detecting and quantifying anti-neutrophil-cytoplasmic antibodies (ANCA) in a sample of bodily fluid from a patient suspected of suffering from an autoimmune disease, comprising the steps: obtaining a predetermined number of human polymorphonuclear neutrophils (PMNs); providing an equivalent number of microspheres of predetermined optical and physical properties; contacting and incubating said predetermined number of human polymorphonuclear neutrophils (PMNs) with said equivalent number of microspheres; inducing formation of extracellular traps (NETs) by said polymorphonuclear neutrophils (PMNs) having antigens recognized by anti-neutrophil-cytoplasmic antibodies (ANCA); allowing interaction of said microspheres and said extracellular traps (NETs) to obtain NET-coated microspheres having entangled antigens recognized by anti-neutrophil-cytoplasmic antibodies (ANCA); contacting said NET-coated microspheres with a sample of bodily fluid, notably a defined serum or plasma sample; creating conditions for interaction of anti-neutrophil-cytoplasmic antibodies (ANCA) with said antigens on said NET-coated microspheres; labeling said anti-neutrophil-cytoplasmic antibodies (ANCA) bound onto said NET-coated microspheres, e.g. by the addition of a second labeled antibody; and analyzing said NET-coated microspheres with labeled anti-neutrophil-cytoplasmic antibodies by flow cytometric methods to determine and/or quantify the amount of anti-neutrophil-cytoplasmic antibodies (ANCA) present in the sample of bodily fluid.

The use of a microsphere-based flow cytometric assay (FCM) provides improved quantitative precision and accuracy compared to visual microscopy and significant labor saving. While methods have been developed to quantify auto-antibodies in bodily fluids and tissue culture samples, including bio- and immunoassays (e.g. ELISA) and PCR, each of these techniques possesses one or more significant limitations. An ELISA will only detect one analyte or one combination of analytes at a time and requires washing steps; PCR does not detect native proteins and auto-antibodies. A microsphere-based flow cytometric assay allows further the use of several uniform microsphere fractions, each associated with another auto-antigen, so that many of the current limitations are overcome. The present technique utilizes one or more fractions of uniform microspheres, each coupled or associated with another potential autoantigen or an isolate comprising several autoantigens and protein-DNA complexes, as support for an autoantibody immunoassay which is followed by flow-cytometric separation, compared to the usual washing steps of an immunoassay, and a quantitative analysis of the labeled microspheres by having those either sorted and analyzed or counted in accordance with the labeling and the optical properties of the microspheres. This technique allows a multiplex analysis based on different antigens for auto-antibodies which may be quantitatively determined severally as to antigen and collectively. In other word, the disclosed system and method facilitates the development of a multiplex assay that simultaneously tests and measures different auto-antibodies in a small sample volume. As the method can be implemented into a rapid assay requiring no differential washing steps, the quantitation of the auto-antibodies in serum or plasma can be done in less time and automatically. The quantitative results are further objective and can be obtained for different auto-antibodies since the microsphere-based flow cytometry allows a simultaneous physical and chemical analysis and separation of different microspheres based on their optical properties. Flow cytometry is already routinely used in the diagnosis of disorders such as blood cancer and widely used for high-throughput quantitative and qualitative sorting and counting of cells, as well as for biomarker detection. As no complex washing steps are required for distinguishing unspecific antibody-binding from a binding of disease-relevant auto-antibodies, the FCM method with microspheres provides a tremendous analytical advantage over conventional immunoassays (ELISA) in addition to the reduced time requirements.

The autoimmune disease diagnosed may be selected from anti-neutrophil cytoplasmic antibodies (ANCA)-associated vasculitides (AAV), granulomatosis with polyangiitis (GPA), microscopic polyangiitis (MPA), eosinophilic granulomatosis with polyangiitis (EGPA), primary pauci-immune necrotizing and crescentic glomerulonephritis, drug-induced vasculitides, cystic fibrosis, inflammatory bowel disease (IBD), primary sclerosing cholangitis, rheumatoid arthritis, systemic lupus erythematosus (SLE) and psoriasis.

While the sample may be blood, serum, plasma, saliva, sweat, tears or stool from a patient suspected of suffering from an autoimmune disease, the preferred sample is serum or plasma.

The microspheres may be polystyrene or latex microbeads, preferably having a diameter from 1 to 10 μm, preferably from 1.5 μm to 66 μm, more preferably from 2 μm to 4 μm. Said microspheres may be labeled with at least one fluorescent dye excitable at a set wavelength. However, the prior art describes numerous types of particles and microspheres that can be sorted and analysed in a flow cytometry. Some reported microsphere-based flow cytometric assays even employ up to one hundred different types of microspheres that are sorted and counted in accordance with their optical and physical properties.

The disclosure further relates to a composition for use in quantifying ANCA in blood or serum by flow cytometry, comprising microspheres as described above which have been associated with ANCA targeting antigens by contact and stimulation of polymorphonuclear neutrophils (PMN).

Another aspect of the disclosure relates to a kit of parts for use in flow-cytometry comprising a pipettable composition of microspheres that have been associated with ANCA targeting antigens as described above, and a composition comprising labeled antibodies specific for human anti-auto antibodies.

The instant disclosure relates to a kit of parts comprising a pipettable composition of microspheres associated with or coupled with one or more ANCA targeting antigens selected from the group comprising proteinase 3 (PR3), myeloperoxidase (MPO), elastase, cathepsin G, lactoferrin, lysozyme, permeability-increasing protein (BPI) or combinations thereof. The antigens or haptens may be associated with one type of microspheres or several types of microspheres to allow for a subtyping of the auto-antibodies. In one embodiment, the microspheres may be coated with the entire cytoplasmic fraction from stimulated polymorphonuclear neutrophils (PMN) or with NETs from stimulated PMN which also contain complexes of chromatin or nucleic acids and cytoplasmic antigens.

The disclosure further encompasses a multiplex immunoassay on the auto-antibodies in serum or plasma which is followed by a microsphere-based flow-cytometric analysis. The specific advantage of the flow-cytometric method lies therein that the washing steps can be omitted and replaced by a selective binding step which is only followed by an automated and quantitative separation of the microspheres based on their optical or physical properties. This distinguishes the instant disclosure from multiplex microsphere-based flow cytometric methods as antigen-coated microspheres and flow-cytometric separation are employed in combination for fishing and quantitation of auto-antibodies in serum (Vignali D A "*Multiplexed particle-based flow cytometric assays*", J Immunol Methods. 2000 S, 243(1-2): 243-55)

The beads or microspheres can be bound to capture reagents such as nucleic acids, oligonucleotides and peptidic antigens, therefore facilitating the quantification of auto-immune antibodies against single antigens as well as of complexes of DNA and proteins. As the microspheres and the cell debris run through the instrument, the internal dyes (e.g. fluorescent groups, etc) are excited by a laser which results in the classification of each microspheres. Another laser may then excite the reporter dye which is then directly proportional to the amount of auto-antibodies or ANCA bound to each bead. The resulting fluorescence is then recorded by the instrument which then provides a median fluorescence unit obtained from measuring 100 beads.

In one aspect the disclosure relates to a use of flow cytometry and a kit of parts as described above for monitoring the efficacy of an immunosuppressing therapy.

In a further aspect the disclosure relates to a use of flow cytometry and a kit of parts as described above for in vitro diagnosis of an autoimmune disease.

Indirect immunofluorescence (IIF) on ethanol-fixed polymorphonuclear neutrophils (PMN) is the current approach for ANCA screening. This method is accompanied by certain downsides, such as the occurrence of false positives as well as a very high inter- and intra-assay variability due to the microscope method. Thus, confirmation by additional methods such as ELISA is needed for comparison of results. Also, the interpretation of the various expression patterns is tedious and requires careful training, in particular, when analyzing multiple samples. Indirect immunofluorescence on object slides is a highly subjective assay and the reliability of the evaluation depends very much on the individual observer. The analysis of the microscopic image by computerized method represents no improvement as the sample preparation is highly variable and non-homogenous. The claimed flow cytometric method on the other hand not only provides a reliable detection and quantification of anti-neutrophil-cytoplasmic antibodies (ANCA) in a sample such as serum or plasma but also produces an automated interpretation of data. The claimed method allows full automation of the assessment for ANCA in serum or plasma, resulting not only in faster and more reliable diagnosis but also in a reduced inter- and intra-assay variability. The physician can now reliably monitor and adapt the immune-suppressive therapy as truly needed by the patient.

The principles of the invention will now be further described by reference to its advantages, representative examples and drawings which shall, however, not limit the gist of the invention. The desired scope of protection can be derived from the disclosure contained in the claims.

BRIEF DESCRIPTION OF THE DRAWINGS

In the accompanying drawings.

DETAILED DESCRIPTION OF THE INVENTION

Figure 1A:
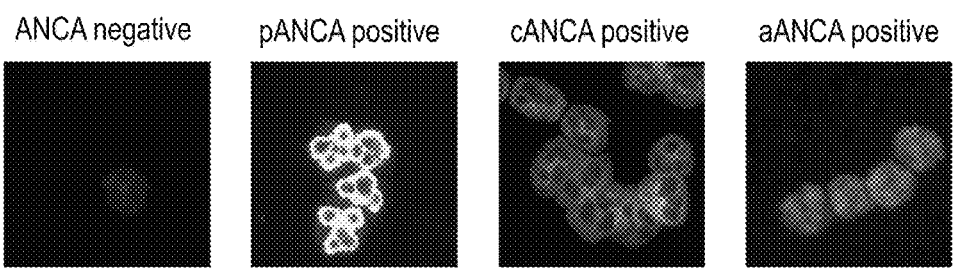
FIGS. 1 A-D are immunofluorescence microscopy images of ethanol-fixed stimulated polymorphonuclear neutrophils (PMNs) and neutrophil extracellular traps (NETs) and stained anti-neutrophil-cytoplasmic antibody (ANCA)

The microscopy images and graphs demonstrate that anti-neutrophil cytoplasmic antibodies (ANCA)-target antigens are present on NETs and that ANCA-target antigen decorated microspheres can be used not only to detect but also to quantify ANCA in serum or plasma using flow cytometry. The novel flow cytometry assay is based on microspheres coupled to ANCA target antigens which may comprise microspheres entangled by complexes of chromatin and cytoplasmic antigens (NET) as well as microspheres coupled to purified PMN cytoplasmic antigens and combinations of ANCA target antigens. ANCA target antigens are inter alia present on proteinase 3 (PR3), myeloperoxidase (MPO), elastase, cathepsin G, lactoferrin, lysozyme, permeability-increasing protein (BPI) and of course combinations thereof and on corresponding DNA-protein complexes. The disclosed microsphere-based flow cytometry assay allows automatable ANCA detection and quantitative determination. It is further suggested to use multiple ANCA-target antigen coupled microspheres for detailed multiplex analysis and quantification of ANCA in serum or plasma.

Quantitative and qualitative analysis of ANCA in serum or plasma provides improved assessment of the stage and severity of the auto-immune disease and the proposed FCM assay may be based on microspheres decorated with whole cytoplasmic PMN antigens as well as DNA-antigen complexes of polymorphonuclear neutrophil granulocytes (PMN). Current immunocytochemical approaches are based on ethanol-fixation procedures and semi-quantitative visual or computerized evaluation of microscopic images.

Anti-neutrophil cytoplasmic antibodies (ANCA) are auto-antibodies targeting cytoplasmic antigens of polymorphonuclear neutrophil granulocytes (PMN) and/or their complexes with chromatin which may arise and become presented during chronic inflammation. This is likely the etiology of a group of autoimmune diseases, referred to as ANCA-associated vasculitides (AAV) which include, while not limited thereto, as representative examples granulomatosis with polyangiitis (GPA), microscopic polyangiitis (MPA) and eosinophilic granulomatosis with polyangiitis (EGPA). AAV are distinguished by an inflammation of small-to-medium-sized blood vessels and therefore a long-term immunosuppressive therapy is indicated to maintain sufficient kidney function. The detection and characterization of ANCA has become an important diagnostic tool for the classification of these diseases, and may be involved in the pathophysiology of many others. Moreover, the ANCA levels in serum or plasma may serve as a prognostic marker regarding disease activity or a possible relapse and determination of the ANCA levels in serum or plasma may be used to monitor the efficacy of the immunosuppressive therapy.

Routine ANCA screening is currently performed on ethanol-fixed neutrophils using indirect immunofluorescence technique. It remains to be elucidated in which way the ANCA target antigens, the cytoplasmic and granular proteins of neutrophils, must be processed to become immunogenic as well as presented to the immune system. Various studies have shown that neutrophils extrude their chromatin decorated with granular proteins, also known as neutrophil extracellular traps (NETs), in response to various stimuli. More precisely, the polymorphonuclear neutrophil granulocytes (PMN) are each capable of decondensing its segmented nucleus via protein citrullination and proteolysis and of releasing its decondensed chromatin which contains or is decorated with granular proteins. Neutrophil extracellular traps (NETs) therefore consist of extracellular strands of decondensed DNA in complex with histones and neutrophil granule proteins. NETs may be generated in nitro by stimulation of isolated neutrophils with substances such as phorbol ester, ionophores, lipopolysaccharide (LPS), components of gram-negative bacteria or interleukin 8 (IL-8), a neutrophil chemoattractant. The induction of NETs by IL-8 and LPS indicates that NETs are formed in vivo during inflammation and infection. In fact, NETs are found in vivo during bacterial infections such as appendicitis. On the other hand, the antibacterial activity of NETs is abrogated by DNase activity. Hence, via NET formation neutrophils expose granular and nuclear content to the extracellular inflammatory milieu and may serve as an immunogenicity platform.

Neutrophils are the most abundant type of white blood cell in humans and have crucial roles in the innate immune response. They act as a first line of defense against invading microorganisms. Neutrophils target microorganisms through a number of processes including degranulation, release of granular antimicrobial peptides (e.g. myeloperoxidase, neutrophil elastase and matrix metalloproteinases), phagocytosis and degradation via synthesis of reactive oxygen species (ROS) inside phagolysosomes. Microbial trapping is carried out by extrusion of a meshwork of chromatin bound to granular peptides, say neutrophil extracellular traps (NETs).

Activated neutrophils undergo morphological changes in order to release NETs. The nuclear and granular membranes disintegrate and elastase enters into the nucleus, followed by hypercitrullination of histones, chromatin decondensation into the cytoplasm, rupture of the plasma membrane, and extrusion of nuclear material from the cell into the extracellular space. The enzymes peptidyl arginine deiminase type IV(PAD4), neutrophil elastase (NE), and myeloperoxidase (MPO) have been implicated in the initial chromatin decondensation and degradation of the nuclear envelope. As a final step, extracellular DNA, histones, and granular enzymes form a network of NETs that entrap endogenous (e.g. platelets) and extrinsic (e.g. bacteria) particles and molecules. The negatively charged DNA acts as the backbone of the NET, interacting with other NET components through positive electrostatic charge.

The formation of NETs constitutes a common event in distinct pathophysiologic conditions. However, the expression of distinct bioactive proteins on NETs in different disorders might determine their specific function in disease pathogenesis. A "two-hit" model has been proposed to explain the differential protein cargo of NETs in distinct disorders. A first "hit" according to the model may be the disease-specific environment that primes neutrophils to express disease-associated proteins. A second "hit" can be responsible for the induction of NET formation.

A number of studies demonstrate that NETs play a driving role in the pathogenesis of a variety of autoimmune disorders, such as systemic lupus erythematosus (SLE), antineutrophil cytoplasmic antibody (ANCA)-associated vasculitis (AAV), rheumatoid arthritis (RA), antiphospholipid antibody syndrome (APS) and psoriasis. Autoimmune diseases are characterized by the circulation of auto-antibodies recognizing intracellular antigens. As mentioned above, NETs are extracellular complexes of components that are normally intracellular, including DNA, histones, and granule proteins. These components are frequent targets for auto-antibodies.

Neutrophils from patients suffering from autoimmune diseases are more prone to undergo NET formation than neutrophils from healthy controls or patients without auto-immune diseases. Thus, NETs are a main source of auto antigens and may be decorated with disease-specific proteins. In turn, various auto-antibodies can promote the release of NETs. In other words, in addition to NETs providing antigens for autoantibody formation, auto-antibodies can induce NETs, therefore, leading to a vicious cycle that propagates inflammation in these disorders.

For example, there is evidence supporting the involvement of NETs in the pathophysiology of systemic lupus erythematosus. It has been shown that NETs are directly associated with the severity and the progression of this disease. There is a disease-associated defect in the clearance of NETs, due to the reduced activity of DNase 1 and increased amounts of DNase 1 inhibitors. Therefore, deregulation of NET clearance may be one of the initial steps leading to lupus-specific autoantibody production.

Even though the list of diseases in which NETs have been identified is extensive, a further characterization of the disease-specific role of NETs in every one of these disorders is required.

Neutrophils from patients with AAV display enhanced NET formation in vitro. In addition, levels of NET remnants, such as MPO-DNA complexes, and neutrophil granular proteins, such as calprotectin (a dimer of S100-A8 and S100-A9), are increased in sera from patients with AAV. High levels of NET remnants are found in patients with high AAV disease activity and high neutrophil count, correlating inversely with levels of ANCA. Furthermore, immunostaining of renal biopsy specimens from patients with AAV revealed the presence of NETs and NET-associated molecules in areas of inflammation, around areas of fibrinoid necrosis in kidneys with necrotizing glomerulonephritis, and along interlobular arterial walls. These observations suggest that NET formation is involved in vascular damage and immune system activation in AAV. Vascular inflammation could thus be initiated and perpetuated by ANCA-induced activation of primed neutrophils and monocytes.

Wegener's granulomatosis (WG) is characterized by expression of anti-neutrophil cytoplasm auto-antibodies to proteinase-3 (PR3). Van Rossum A P et al ("*Human anti-neutrophil cytoplasm auto-antibodies to proteinase-3 (PR3-ANCA) bind to neutrophils*", Kidney Int. 2005 August; 68(2):537-41) observed increased binding of anti-neutrophil cytoplasm auto-antibodies from proteinase-3 (PR3-ANCA)-positive samples to polymorphonuclear neutrophil granulocytes (PMN), as compared to healthy controls. Immunocytochemical analysis for PR3 and IgG demonstrated that IgG in plasma or serum from PR3-ANCA-positive patients bound to PMN expressing PR3 but not to PMN lacking PR3 expression on their membrane.

In around 90% of granulomatosis with polyangiitis (GPA) patients, a cytoplasmic ANCA pattern (cANCA) is detectable, showing a diffuse cytoplasmic fluorescence with interlobular accentuation that spares the nucleus. GPA-associated cANCA most often exhibit a specific affinity for proteinase 3 (PR3), a serine proteinase typically present in azurophilic granules of polymorphonuclear neutrophil granulocytes (PMN) (Gross et al. 1993).

On the other hand, a perinuclear ANCA pattern with possible nuclear extension is detected (pANCA) with samples from patients suffering from microscopic polyangiitis (MPA) and eosinophilic granulomatosis with polyangiitis (EGPA). Myeloperoxidase (MPO), the most common underlying antigen in MPA and EGPA, is also found in neutrophil granules. Besides AAV, pANCA are found in other diseases, including autoimmune-hepatitis, primary sclerosing cholangitis and inflammatory bowel diseases. Interestingly, MPO immunoreactivity does not seem to account for most of non-vasculitic pANCA.

ANCA fluorescence in non-AAV sera may also depict a mix of perinuclear and cytoplasmic fluorescence. These atypical fluorescence patterns are, therefore, called aANCA. The prevalence of p/aANCA in ulcerative colitis (UC) has been reported as high as 80%, which implies a broad relevance for the nature of this disease.

However, the impact of ANCA in ulcerative colitis (UC) is unclear and UC-associated ANCA might differ from AAV-associated ANCA in important characteristics such as a broader antigen specificity and the presence of complex antigens, like DNA-protein complexes, improved detection methods could increase the usefulness of p/aANCA in understanding their specific contribution to the disease.

Analysis of sera from patients with systemic lupus erythematosus (SLE), rheumatoid arthritis (RA), Felty's syndrome (FS), and anti-neutrophil cytoplasmic antibody-associated vasculitides (AAVs) using confocal microscopy, enzyme-linked immunosorbent assay (ELISA) and Western blotting is described in Dwivedi N et al ("*Felty's syndrome autoantibodies bind to deiminated histones and neutrophil extracellular chromatin traps*" Arthritis Rheum. 2012 April; 64(4):982-92). Sera were tested for binding to activated neutrophils, deiminated histones, and neutrophil extracellular chromatin traps (NETs). Circulating auto-antibodies in Felty's syndrome are preferentially directed against protein arginine deiminase (PAD)-4-deiminated histones and bind to activated neutrophils and NETs. Neutrophil activation and the production of NET-associated nuclear auto-antigens are related to increased reactivity with modified auto-antigens in the initiation or progression of Felty's syndrome.

Sera from patients suffering from either ANCA-associated vasculitis (AAV), ulcerative colitis (UC) or sera from patients without diagnosed ANCA-associated diseases were respectively subjected to either conventional indirect immunofluorescence on ethanol-fixed cells or flow cytometric ANCA detection employing microspheres according to the disclosure.

ANCA-related immunofluorescence was readily detectable on ethanol-fixed neutrophil extracellular traps (NETs), demonstrating that NETs are structures comprising ANCA target antigens. Importantly, we observed that neutrophils form NETs in response to microspheres and stick to the surface of these spheres. Thus, this approach allows simultaneous stimulation of polymorphonuclear neutrophil granulocytes (PMNs) and provides a scaffold for handling NETs, which are otherwise difficult to manipulate. A coating of the microspheres is taking place as the neutrophils are contacted by the microspheres, so that a platform for easy handling of NETs and efficient antigen presentation for further analysis is provided. Therefore, in a single step and without the use of chemical compounds, stimulation of NET formation and controlled handling of NETs for quantitative analysis is rendered possible. Using NET-coated microspheres in flow cytometry, we were capable to reliably detect different ANCA, regardless of their immunofluorescence patterns, p-ANCA (perinuclear), c-ANCA (cytoplasmic) and a-ANCA (atypical) in tested patient sera. Therefore, the present method allows for automatable classification of ANCA-related diseases based on their ANCA expression pattern. According to the present disclosure, uncoated and NET-coated microspheres may be commercially developed as a novel tool for automated flow cytometric ANCA screening assays.

In vitro stimulation of polymorphonuclear neutrophil granulocytes (PMN) is known in the prior art, for example, by addition of chemical phorbol 12-myristate 13-acetate or calcium-ionophore to the culture medium. As a result, neutrophils may produce and release neutrophil extracellular traps (NETs). However, the composition of NETs is complex and so far not fully determined. It must be accepted that different stimulation approaches may result in distinct protein expression patterns, including antigens recognized by auto-antibodies. Accordingly, the stimulation approach must be carefully designed so as to promote presentation of the specific antigens on NETs. Important factors are duration and nature of stimulus (chemical and physical), which must be combined in an appropriate manner in order to obtain the right panel of antigens released by the stimulated neutrophils.

As far as known, the prior art does not disclose any means that allow handling of NETs, which are difficult to manipulate as they have a natural tendency to stick to certain plastic or glass surfaces, so that isolation or recovery of NETs has so far been difficult. Thus, a reliable isolation method of this biological material is not available, let alone a method for analysis of NETs and NET-related proteins by flow cytometric approaches, which require suspension and controlled handling of the biological material. These disadvantages can be overcome by the method of the disclosure, which comprises the use of polystyrene microspheres of predetermined size. By use of the microspheres according to the disclosure, the use of chemical compositions is prevented, which use could potentially alter the antigen expression pattern of NETs. With the present method, a set of antigens recognized by ANCA may be consistently stimulated, isolated and rendered susceptible for flow cytometric analysis in a single step by using microspheres according to the disclosure.

Further, the microspheres of the present method are contacted with the neutrophils to be stimulated in a predetermined number. In a preferred embodiment, the number of microspheres corresponds to the number of isolated neutrophils. An optimal NET-release by neutrophils and NET-coating of the spheres may thereby be achieved. Alternative, PMNs to microspheres 1:2 ratio may also be applied.

To demonstrate the suitability of the present method for detection of anti-neutrophil cytoplasmic antibodies (ANCA), sera of patients suffering from ANCA-associated vasculitides (n=10), ulcerative colitis (UC: n=30) or a control group that did not suffer any ANCA-related diseases (n=20) were used. We performed conventional indirect immunofluorescence (IIF) on ready-to-use test kits containing ethanol-fixed polymorphonuclear neutrophil granulocytes (PMN) on slides to screen the available sera for ANCA by routine clinical diagnostics.

FIGS. 1A-1D show microscopy images depicting the detection of ANCA fluorescence and auto-antigens on both ethanol-fixed polymorphonuclear neutrophil granulocytes (PMN) and NETs. The different patterns of ANCA-positive test sera can be observed after indirect immunofluorescence (IIF) on ethanol-fixed PMN, resulting in the described ANCA classification, while negative sera gave no significant fluorescence signal (see FIG. 1A). pANCA showed a perinuclear, rim-like pattern, cANCA a cytoplasmic pattern and the depicted aANCA a mix of nuclear and cytoplasmic fluorescence (tested sera: n=10 AAV sera, n=30 UC sera, n=20 control sera; ANCA positivity in AAV; 100%, in IBD: 55%, in control: 20%).

Figure 1B:
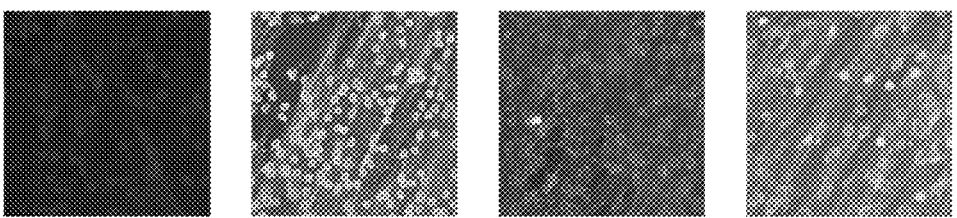
Figure 1C:
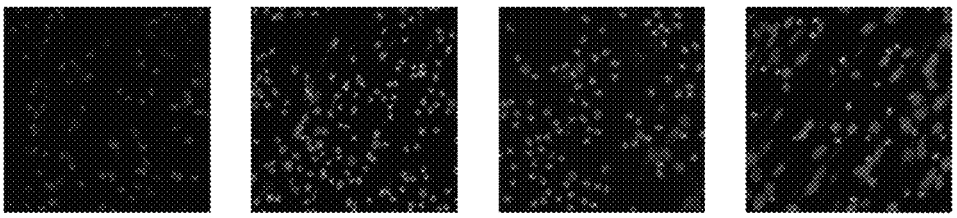
Figure 1D:
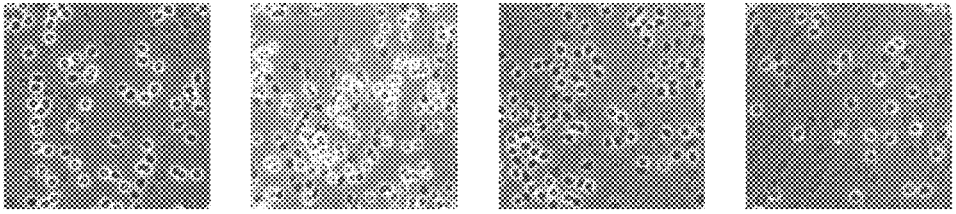

Propidium iodide was used as a counterstain for NET-indirect immunofluorescence to show DNA-ANCA colocalization (see FIG. 1C). Indeed, a colocalization was observed. ANCA immunofluorescence, however, has an increased sensitivity and more readily displays the extracellular fibrous structure of NETs. Phase contrast microscopy of these culture slides is included to show that NET cultures include both intact cells and extracellular neutrophil-derived content (see FIG. 1D).

Sera from controls mostly showed no detectable immunofluorescence on neutrophil substrate slides (disease control sera tested ANCA positive; n=4/20). Sera from patients with ANCA-associated vasculitis showed either a perinuclear or a cytoplasmic staining pattern, respectively, whereas ANCA in sera derived from patients with UC showed various staining patterns, including perinuclear, nuclear or atypical staining patterns (ulcerative colitis (UC) sera tested ANCA positive: 63%).

In order to analyze whether ANCA auto-antigens are present on NETs, we generated NET-substrate slides by stimulating freshly isolated polymorphonuclear neutrophil granulocytes (PMN) in HBSS-based buffers with a mildly skewed sodium bicarbonate/$pCO_2$ ratio (30 mM/5% $CO_2$) (Leppkes et al. 2016; Maueroder et al. 2016) for 120 minutes followed by ethanol fixation to mimic the conditions of conventional ANCA screening kits.

FIG. 1B shows indirect immunofluorescence performed on ethanol-fixed NETs using patient sera and anti-human-IgG-fluorescein conjugates. Representative images show a higher intensity of fluorescence on NETs treated with pANCA-, cANCA- or aANCA-positive sera, as compared to ANCA-negative sera. It can be appreciated with surface staining that NETs and their fibrous macrostructure surround intact PMN. Interestingly, ANCA-binding to NETS was readily detectable using secondary anti-human IgG-Fluorescein conjugate. ANCA-negative sera largely showed markedly reduced fluorescence intensity on NETs as compared to ANCA-positive sera. This effect was detectable for pANCA, cANCA and aANCA.

Thus, NETs appear to be structures carrying auto-antigens. However, unspecific binding of IgG to ethanol-fixed NETs was repeatedly observed, even with sera independently tested negative for ANCA, indicating that the conventional approach may frequently lead to false positives.

The inventors have therefore examined whether fluorescence signal intensity measurement in state-of-the-art flow cytometers is superior to microscopic fluorescence detection on slides with ethanol-fixed polymorphonuclear neutrophil granulocytes (PMNs). However, NETs are fragile, vary significantly in size, easily aggregate or dump and are, thus, not suitable for flow cytometric studies per se. In order to be able to manipulate and adapt NETs for use in flow cytometric analysis, polystyrene microspheres with an average size of 3 μm were used. Freshly isolated PMNs were incubated with polystyrene microspheres, which in turn triggered NET formation and release.

Figure 2A:
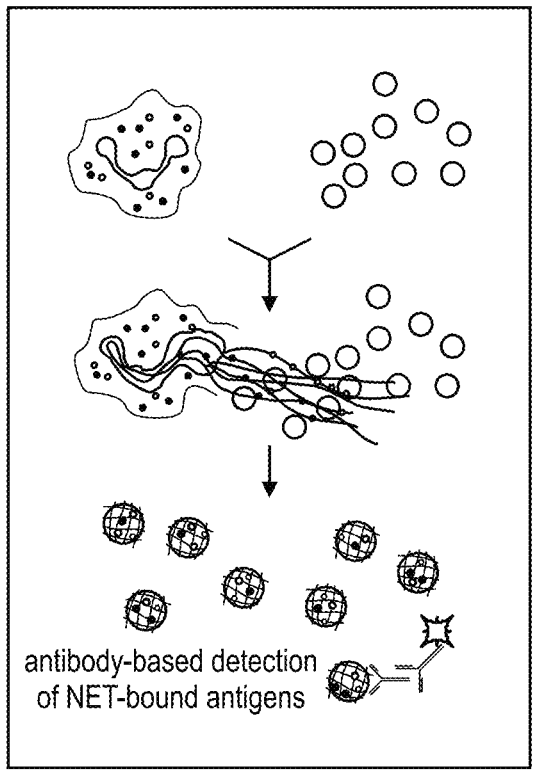
FIG. 2 A,B a schematic drawing (A) of the principle of neutrophil extracellular trap (NET) formation and the coating/decoration of microspheres with antigen; and (B) corresponding micrographs of neutrophil extracellular traps (NETs) that are decorated with entangled granular and nuclear content.
Figure 2B:
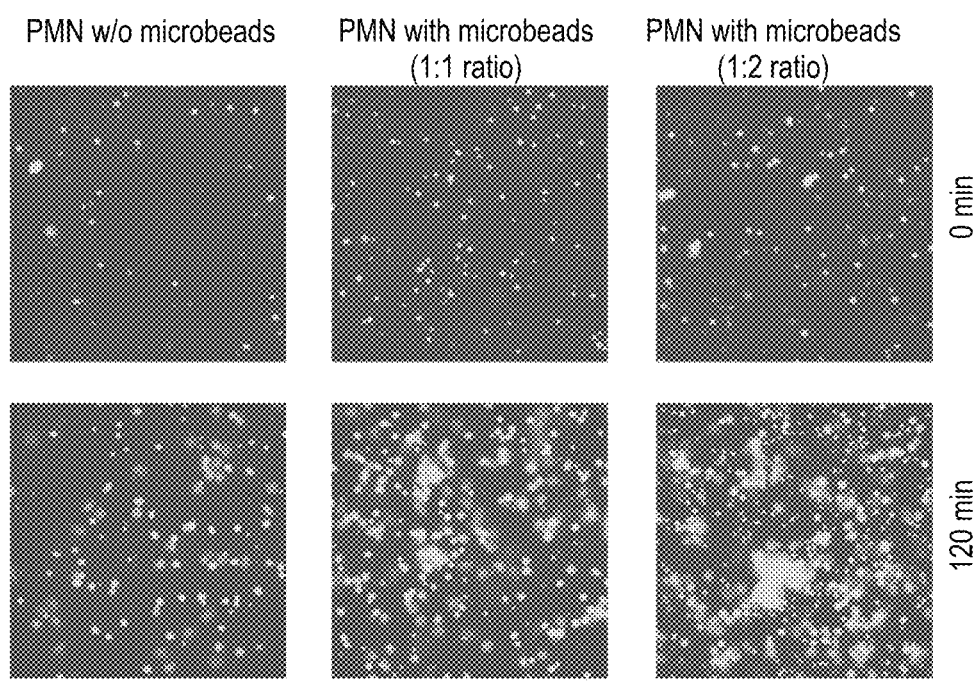

NETs produced by contacting polymorphonuclear neutrophil granulocytes (PMNs) with polystyrene were decorated with anti-neutrophil cytoplasmic antibodies (ANCA)-target proteins adhered to the surface of the polystyrene microspheres. FIG. 2A shows a model of microbead-induced NET formation upon co-culturing polystyrene microspheres and PMNs. FIG. 28 shows that microbead-induced NETs are decorated with granular and nuclear content (e.g. neutrophil elastase, myeloperoxidase and citrullinated histone H3 are depicted as bright-fluorescent-dots) and remain bound to the microbead surface, resulting in NET-coated microspheres. Consequently, these NET-bound antigens may be detected by means of specific, primary antibodies or ANCA-positive sera. NET-coated microspheres are therefore suitable for flow-cytometric analysis of ANCA.

Figure 3A:
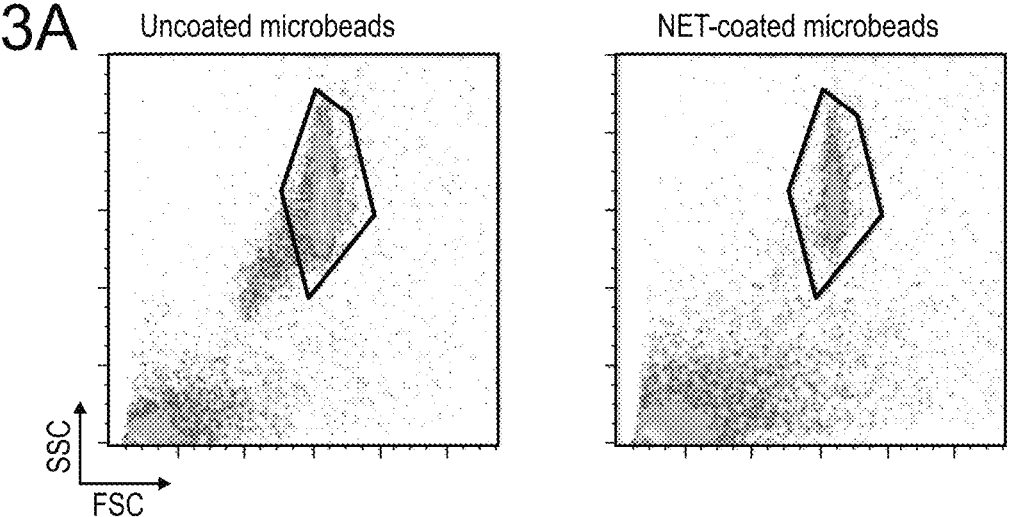
FIG. 3 A,B are plots (A) of the size and granularity of uncoated and NET-coated microspheres; and (B) graphs showing a flow cytometric analysis of DNA and NET-related proteins on NET-coated microspheres using different staining methods.
Figure 3B:
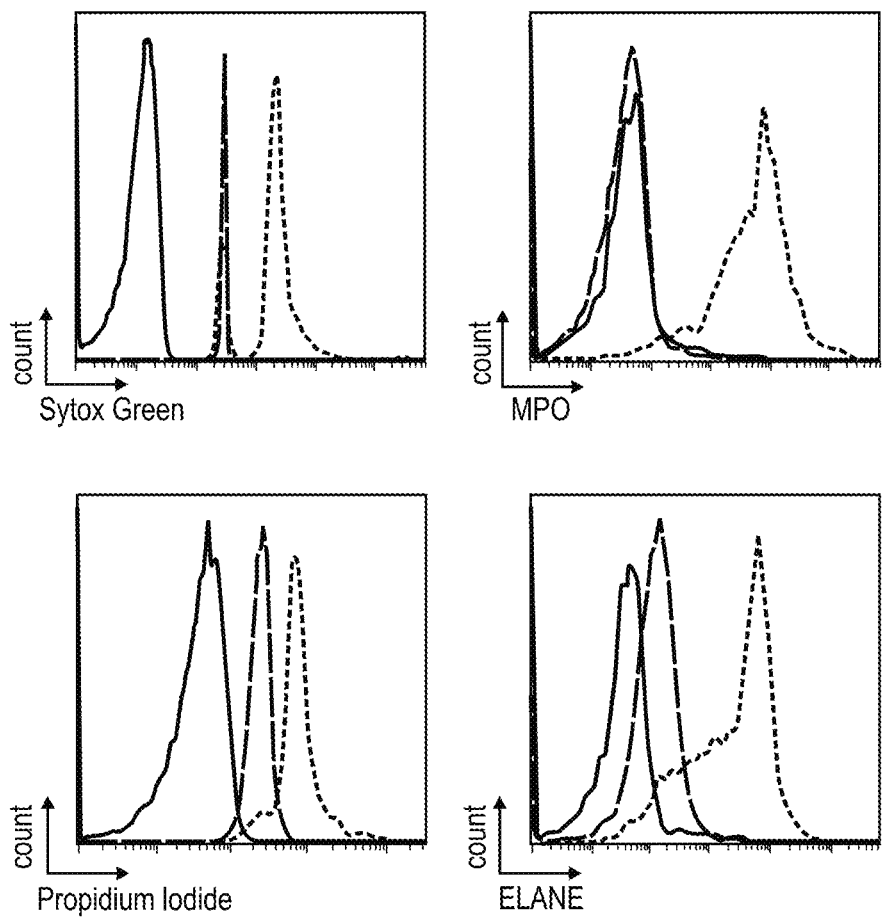

FIGS. 3A-3B show detection of DNA and NET-related proteins on coated microspheres. The NET-coated microspheres are stable in size and granularity. Microspheres were, hence, easily identified in FSC/SSC (forward scatter (FSC) vs. side scatter (SSC) plots due to their distinct size and granularity as shown in FIG. 3A. NET-coating of microspheres did not alter microbead's size or granularity (representative image of n>40 independent experiments). In the experiments shown in FIG. 3B, NET-coated spheres were processed as described in FIG. 3A and subjected to flow cytometry. Employing DNA-intercalating dyes like Sytox Green and propidium iodide, extracellular NET-derived DNA was readily detected on the coated spheres. Neutrophil elastase (ELANE) and myeloperoxidase (MPO) were also readily detected by flow cytometry, thus, demonstrating the development of a successful NET-coating process of polystyrene microspheres (n>6 independent experiments).

Figure 4A:
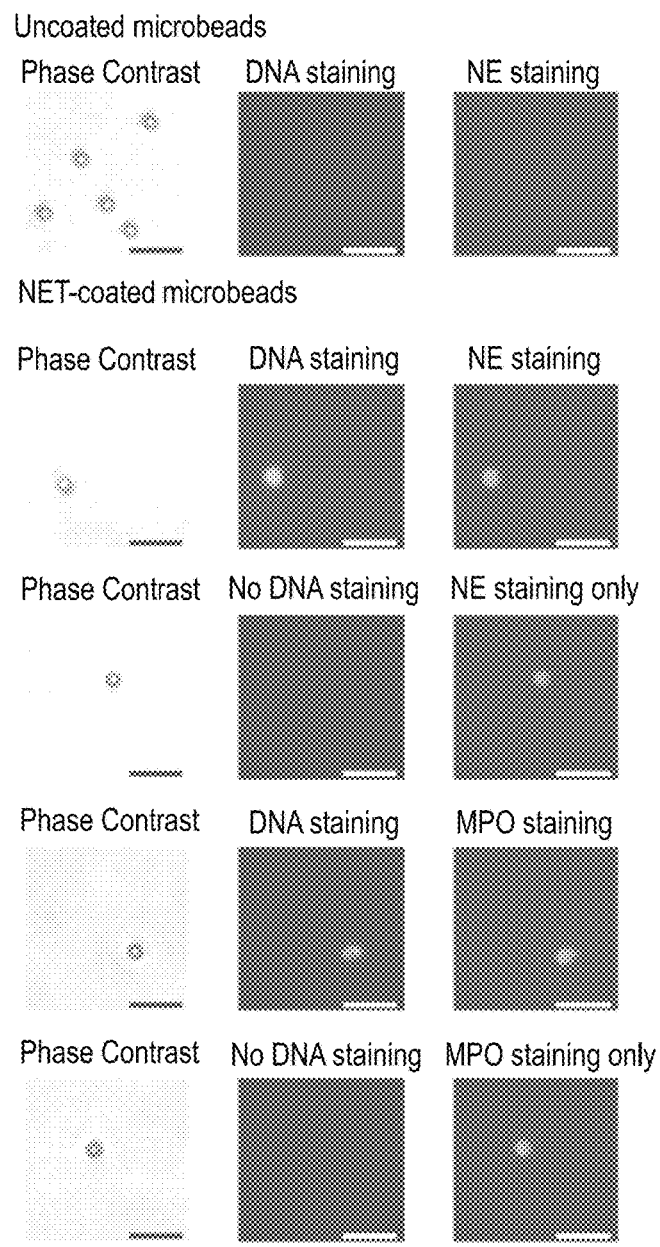
FIG. 4 A,B are (A) micrographs showing a staining of DNA and NET-proteins on uncoated and NET-coated microspheres; and (B) graphs showing antibody-based ANCA detection in ANCA-positive and -negative sera as well as in controls.

NET-coated microspheres were subjected to indirect immunofluorescence using sera from patients and controls and the detection of bead-bound ANCA by secondary fluorescence linked mouse anti-human IgG. In further microscopic and flow cytometric analyses of microspheres, we specifically detected the presence of DNA and neutrophil-derived proteins such as neutrophil elastase (NE) and myeloperoxidase on NET-coated microspheres. Uncoated and NET-coated spheres were subjected to phase contrast (PCM) and fluorescence microscopy and the results are shown in FIG. 4A. After employing the DNA-specific dye Sytox Green and primary antibodies for neutrophil elastase (NE) and myeloperoxidase (MPO), visualized by secondary Alexa 555-labeled anti-rabbit, specific positive signals were detected on NET-coated microspheres (n=3 independent experiments).

After having established NETs as a structural platform for ANCA-target antigens and the coated microspheres as a carrier for flow cytometric analysis, we used the newly developed NET-coated microspheres as a substrate for flow cytometric ANCA detection. ANCA could be detected in ANCA-positive sera using NET-coated microspheres.

Indirect immunofluorescence using patient-derived ANCA-positive and -negative sera and a secondary anti-human-IgG Fluorescein conjugate was performed on NET-coated microspheres. Fluorescent intensity did not differ between coated spheres subjected to ANCA-negative serum or fluorescence-linked mouse anti-human IgG secondary antibody, or coated spheres without contact to patient sera and incubated with secondary antibody only.

Figure 4B:
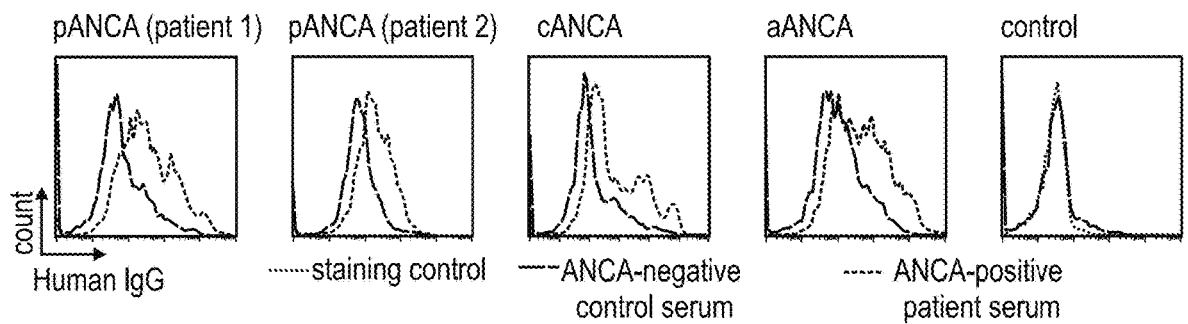

Flow cytometric antibody-based ANCA detection was performed using various ANCA-positive sera, including pANCA, cANCA and aANCA and it is shown in FIG. 4B. The positive sera all had detectably higher mean fluorescence intensities in flow cytometry than the corresponding negative control serum (n>13 independent experiments). Mean fluorescent intensity evoked by ANCA sera was consistently higher than by ANCA-negative sera. In each test run, we included confirmed ANCA-negative sera along with the other samples to account for inter-assay variations. These negative sera consistently showed similar fluorescence intensity as coated spheres that had not been subjected to patient serum incubation (control), applying only secondary fluorescence-linked antibody (see FIG. 4B).

Yet, if coated spheres were incubated with ANCA-positive sera and then analyzed by flow cytometry, a stronger fluorescence intensity was detected compared to the described negative controls. It can therefore be stated that coated spheres offer a possibility to study and detect ANCA in patient sera by reliably discriminating between ANCA-negative and -positive samples. Our newly established method is also able to clearly detect both pANCA and cANCA, although specific fluorescence intensity in cANCA-positive samples appeared to be slightly lower (see FIG. 4B). These experiments demonstrate that the method of the disclosure, comprising the use of NET-coated microspheres, allows for reliable analysis of NETs and NET-related biomarkers by flow cytometry.

For the most common ANCA targets, MPO and PR3, direct ELISA-based detection is available and routinely used in laboratory diagnostics. In particular, atypical ANCA in ulcerative colitis (UC) are reportedly targeting complex antigens such as DNA-protein complexes. ANCAs directed against neutrophil DNA-protein complexes therefore represent true "NET-ANCA" and they are not as readily accessible to direct ELISA-based detection. It has been previously observed, that UC-related NET-ANCA immunofluorescence is strongly reduced after incubation of substrate slides with DNase-1. In agreement with these observations, we detected that NET-ANCA-specific fluorescence vanished after treatment with DNase-1 prior to performing indirect immunofluorescence in conventional ANCA screening with ethanol-fixed PMN (Data not shown).

Figure 5A:
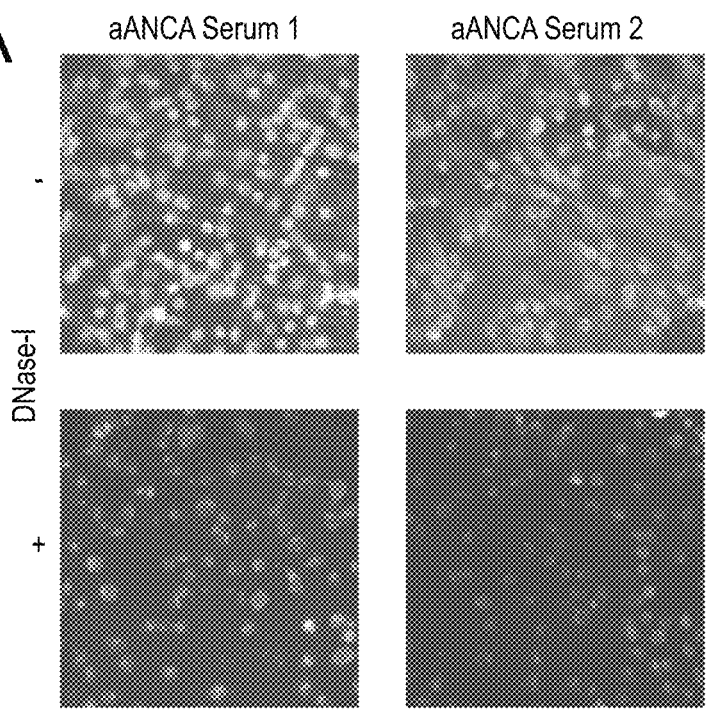
FIG. 5 A,B are (A) microscopy images showing the effect of DNase-1 on ANCA fluorescence in ethanol-fixed neutrophil extracellular traps; and (B) graphs showing the effect of DNase-1 on ANCA fluorescence on NET-coated microspheres analyzed by flow cytometry.
Figure 5B:
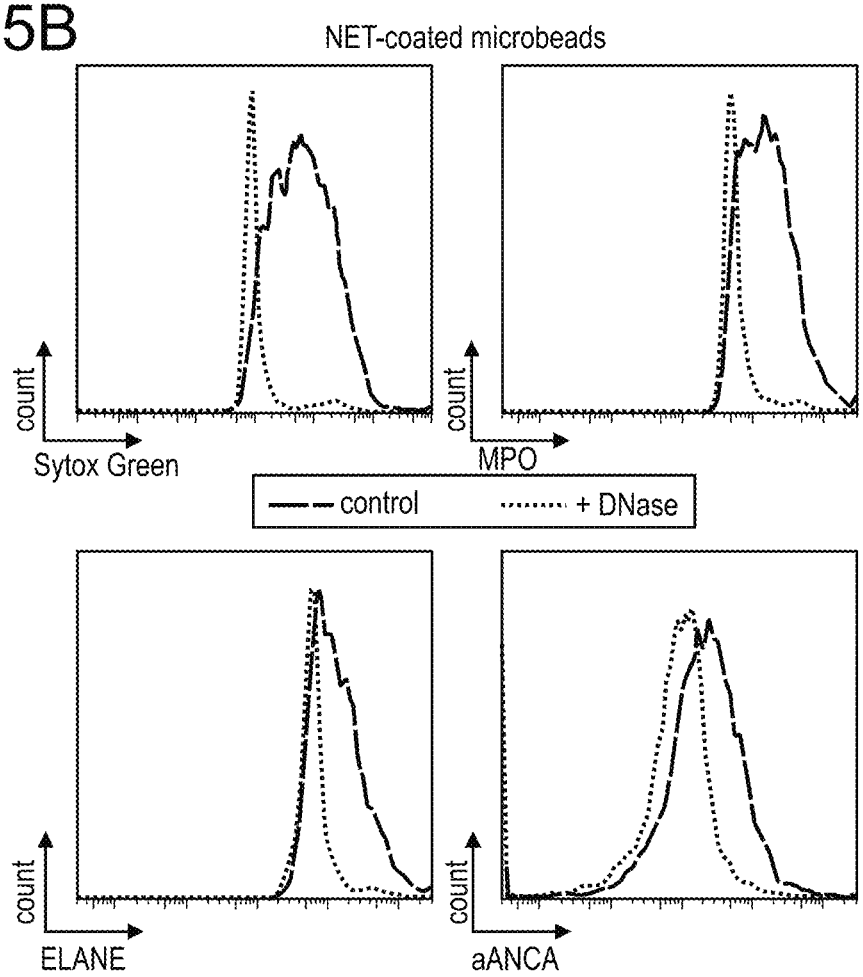

The effect DNase-1 on the detection of inflammatory bowel disease (IBD)-related ANCA on ethanol-fixed neutrophils is shown in FIGS. 5A-5B. Indirect immunofluorescence was performed on ethanol-fixed neutrophil substrate slides using sera positive for IBD-related pANCA and anti-human IgG-fluorescein conjugate after incubation with or without DNase-1 (100 µg/ml) for 60 minutes. Incubation with positive UC-related pANCA sera resulted in a clearly visible fluorescence, while DNase-1 treatment prior to testing resulted in the loss of the specific fluorescence (data not shown).

We argue that chromatin of NETs is a structural extracellular element allowing persistence of ANCA target antigens. The reported surface-bound ANCA-specific staining of activated or apoptotic neutrophils might in part be mediated by chromatin. We therefore performed ANCA immunofluorescence on ethanol-fixed NETs with and without prior DNase-1 digestion (AAV-associated ANCA).

In FIG. 5A, indirect immunofluorescence was performed on ethanol-fixed NETs using sera positive for AAV-related ANCA and anti-human IgG-fluorescein conjugate after incubation with or without DNase-1 (1 µg/µl) for 20 minutes; NETs displayed strong immunofluorescence in response to ANCA-positive patient sera. DNase-1 incubation, however, was able to efficiently remove NET fluorescence (n=3 independent experiments). Interestingly, not only the fluorescence of NETs vanished, but also the signal of intact cells mingled within NETs was reduced. Hence, ANCA-specific surface staining is, in part, mediated by NETs sticking to the surface of cells.

We continued to study the effect of DNase-1 on ANCA detection on NET-coated microspheres in flow cytometry and the results are shown in FIG. 5B. NET-coated microspheres were incubated with DNase-1 and then subjected to Sytox Green and specific immunostainings. A marked reduction in specific fluorescence intensity for DNA, neutrophil elastase (NE) and myeloperoxydase (MPO) was observed after DNase-1 treatment, indicating a removal of both DNA and neutrophil-derived target antigens (n>3 independent experiments). Thus, DNase-1 was able to degrade DNA on coated microspheres. Moreover, after DNase-1 treatment, neutrophil protein-(MPO, NE) and ANCA-specific immunofluorescence of coated microspheres was markedly reduced as determined by flow cytometric analysis.

In conclusion, extracellular chromatin emerges as an important structural surface for ANCA-associated antigen recognition in ulcerative colitis (UC) as well as ANCA-associated vasculitides (AAV).

We aimed to uncover the diagnostic value of NETs in ANCA detection. We observed that NETs are, in fact, decorated with auto-antigens and can serve as a tool in ANCA detection. Despite remaining the recommended method for ANCA screening, indirect immunofluorescence on ethanol-fixed polymorphonuclear neutrophil granulocytes PMN is accompanied by certain downsides such as the occurrence of frequent false positives. Also, interpretation of the various expression patterns requires time and careful training. Moreover, indirect immunofluorescence is a highly subjective test and it is, therefore, dependent on the individual observer.

Standardization of substrates, fixation methods and test procedures are critical issues. After all, these weaknesses of conventional ANCA indirect immunofluorescence contributed to the need for a second confirmation test, namely, specific antigen-dependent ELISA methods that were established for MPO-ANCA and PR3-ANCA detection. These methods do not eliminate the need for indirect immunofluorescence-dependent ANCA screening, as the mentioned target antigens account for only a fraction of all detectable ANCA. In a large patient cohort, myeloperoxydase MPO served as the underlying antigen for only 16% of all detectable pANCA (Tsiveriotis et al. 2011).

In high-throughput clinical diagnostic laboratories, it is desirable to replace indirect immunofluorescence-dependent ANCA screening by an automated methodology for objective assessment. Especially in the setting of a screening test, the simultaneous analysis of multiple samples is desirable and hardly achievable by observer-dependent microscopic analyses.

A flow cytometric method superior to conventional indirect immunofluorescence ANCA-detection and -microscopic evaluation is disclosed herein. The present method prevents the disadvantages of manual evaluation of microscopic samples, delivers objective quantitative values, allows direct interpretation and is accessible to algorithm-based detection approaches.

In summary, we made use of the NET-inducing property of microspheres in order to develop NET-coated microspheres suitable for flow cytometric analysis. After co-incubation of microspheres with living neutrophils, neutrophil-derived DNA and proteins were detected on the microspheres. Moreover, ANCA-specific immunofluorescence was readily detectable on NET-coated microspheres. NET-coated microspheres allowed for reliable distinction of ANCA-positive and -negative patient sera. This demonstrates the suitability of the disclosed microbead-based method for ANCA detection as an alternative to conventional microscopic ANCA screening.

In order to reduce clumping and formation of large aggregates during the coating process of the microspheres, these were rocked at slow motion and, in a later step, mechanically singularized by gentle pippeting. NETs are sticky structures; however, it appears that the use of polystyrene microspheres of predetermined size, in equivalent number with respect to the isolated PMNs, increases capturing/adhering of NETs onto the microspheres, while reducing the interaction of NETs fragments to each other or to the culture dish.

Several microbead sizes, from 1 μm to 20 μm, were tested. It was concluded that particles of sizes greater than 10 μm increased dumping and aggregation, which could be easily distinguished by flow cytometry from single microspheres via their distinct characteristics in FSC/SSC (forward scatter (FSC) vs. side scatter (SSC) plots.

Thus, the use of polystyrene material allows handling of NETs, which otherwise, due to their sticky and stringy nature could only be analyzed on object slides by immunocytochemistry, previous ethanol-fixation. Despite the difficult-to-handle properties of NETs, the use of polystyrene microspheres according to the disclosure makes antigenic material from neutrophils available for both immunostaining and flow cytometric analysis. This, in turn, provides with an easy adaptation to automatable procedures for ANCA determination, objective data collection and straight-forward evaluation of data by algorithm-based approaches. Diagnosis of autoimmune diseases can thereby be performed by automated devices and yield quantifiable ANCA values, improving clinical assessment of the disease's stage and severity. Notably, it opens the possibility for discerning among different diseases, based on their different antigen expression patterns, which can be now assessed in an observer-independent manner, thus, increasing reliability of diagnosis.

If a standardized clinical assay is to be developed, internal controls of ANCA-negative sera are desirable. A cut-off for ANCA-positivity may easily be definable and achievable in automated systems. A second set of internal controls could consist of microspheres coated with HepG2 cellular lysates. HepG2-coated spheres could serve as a reliable internal control to distinguish possible signal overlay of anti-nuclear antibodies (ANA) typical of systemic lupus erythematosus (SLE). HepG2 cells are already being used in some routine laboratories as part of the screening by indirect immunofluorescence ANCA kits.

Some reported differences in antigen detection might be owed to a different isoelectric point (pi) of MPO and PR3. In this regard, the less cationic pI of the cANCA antigen PR3 would result in a weaker DNA-binding to NETs. Please appreciate the distribution of the isoelectric points (pI) of the neutrophil proteins. The less cationic pI of the cANCA antigen PR3 could possibly result in a weakened DNA-binding to the NET. We observed a weaker fluorescence intensity of cANCA-positive sera in our flow cytometric ANCA detection method as compared to pANCA. Improved control of the experimental pH by the addition of HEPES during the coating process resulted in a better detection of cANCA (data not shown).

Therefore, we provide a proof-of-concept of a novel approach to automatize indirect immunofluorescence-ANCA screening by use of NET-coated polystyrene microspheres in flow cytometric methods.

EXAMPLES

Example 1 Detection of Anti-neutrophil-cytoplasmic Antibodies (ANCA) In Human Serum By Flow Cytometry Polymorphonuclear neutrophil (PMN) isolation: Human blood samples were obtained from healthy donors after ethical approval and informed consent using EDTA-coated tubes (S-Monovette® K3E, Sarstedt, Nůmbrecht, Germany). After adding 20 ml PBS, the suspension was gently applied on top of 10 ml Pancoll human (PAN-Biotech, Aidenbach, Germany). Cells were subjected to centrifugation without brakes for 20 min at room temperature at 1800 rpm. The upper layers were discarded, leaving only the lowest layer containing polymorphonuclear neutrophils (PMNs) and erythrocytes followed by 1% dextran sedimentation for 40 minutes (Dextran 500, Carl Roth, Karlsruhe. Germany). PMNs were collected from the supernatant. To further reduce erythrocyte contamination, two cycles of hypotonic lysis were performed. Cells were quantified employing a hemocytometer and finally isolated PMN were put in 1 ml bicarbonate-free Hank's balanced salt solution (HBSS) without calcium and magnesium until further use.

Coating microspheres with neutrophil extracellular traps (NETs): Equal numbers of microspheres (Polybead® Polystyrene 3.0 Micron Microspheres, Polysciences, Valley Road, USA) and PMN were incubated in HBSS with 2 mM calcium and 4 mM bicarbonate/5% CO2 at 37° C. for 2 h. The coated microspheres were then washed twice with PBS and stored at −20° C. until further use.

Immunofluorescence: Patient sera from patients suffering from ANCA-associated vasculitides (n=10), ulcerative colitis (UC: n=30) or a control group that did not suffer any ANCA-related diseases (n=20) were added (diluted 1:10 in PBS) to fixed NETs on culture slides, followed by gentle washing using PBS and application of Kallestad® ANCA Anti-Human IgG Conjugate (Bio-Rad) for fluorescence-labeling. Propidium Iodide Staining Solution (BD Biosciences, San Jose, USA) was employed as a counterstain for DNA. Results were then examined by fluorescence microscopy (DMI 4000B, Leica). Coated microspheres were stained for DNA using Sytox® Green nucleic acid stain (life technologies corporation, Eugene, USA, 1:2000). Primary rabbit-derived antibodies specific for neutrophil elastase (NE) (ab21595, Abcam, Cambridge, UK, 1:400) and myeloperoxydase (MPO) (ab9535, Abeam, 1:200), consequently secondary Alexa 555-conjugated goat anti-rabbit antibodies (ab150090, Abcam, 1:200) were used. Samples were then subjected to fluorescence microscopy (DMI 4000B, Leica) and flow cytometry (BD Accuri C6 flow cytometer system, BD Biosciences), respectively.

Flow cytometric microbead-based ANCA detection: The patient sera described above were subjected to a newly developed ANCA detection method employing flow cytometry and microbead technology. First, the NET-coated microspheres were placed into blocking solution containing PBS and bovine serum albumin 1% (Fraction V. Cart Roth) to reduce unspecific background binding to microspheres. The microspheres were washed with PBS and, then, patient sera (1:10) added and incubated for 30 min. After another washing step, directly labeled Alexa 468 mouse anti-human IgG antibody (Bio Legend, San Diego, USA, 1:200) was added and incubated for 20 min. These stained microspheres were analyzed in a flow cytometer according to the manufacturer's instructions (BD Accuri C6 flow cytometer system, BD Biosciences).

Reagents were purchased from Sigma-Aldrich/Merck (Darmstadt, Germany) unless stated otherwise. Data analysis and figure preparation was performed using FlowJo 7.6.5. Adobe Creative Suite 5 and the Microsoft Office Suite 2010.

Example 2 Indirect Immunofluorescence On Ethanol-fixed Polymorphonuclear Neutrophils Commercial ANCA test kits: Sera from patients suffering from AAV (n=10), UC (n=30) or patients without any ANCA-associated diseases (n=20), respectively, were subjected to indirect immunofluorescence ANCA testing. For this purpose, ethanol-fixed polymorphonuclear neutrophils (PMNs) on object slides were used which had been prepared beforehand (Kallestad® Anti-Neutrophil Cytoplasmic Antibodies Ethanol IFA, Bio-Rad, Hercules, USA; EUROPLUS Granulocyten-Mosaik 32. EUROIMMUN Medizinische Labordiagnostik AG, Lübeck, Germany). Following manufacturer's instructions, tested sera were diluted and incubated on the substrate slides. In a second step, a secondary fluorescence-linked antibody conjugate was applied. The fluorescence patterns were examined by fluorescence microscopy (DMI 4000B, Leica, Wetzlar, Germany).

Neutrophil extracellular trap (NET) stimulation and fixation: For NET stimulation, freshly isolated PMN were seeded on culture Slides (Corning Inc., Big Flats, USA). Cells were incubated at 37° C. for 2 h in HBSS with 2 mM calcium and a bicarbonate/$pCO_2$ ratio of 30 mM bicarbonate/5% $CO_2$ to induce NET formation. Subsequently, ice cold ethanol 95% was used for fixation at −20° C. After removing ethanol, the slides were allowed to dry at room temperature for 20 min.

Example 3 Effect of DNAse on ANCA Detection

DNase-1 treatment: Ethanol-fixed polymorphonuclear neutrophils (PMNs) on ANCA test slides (Kallestad® Anti-Neutrophil Cytoplasmic Antibodies Ethanol IFA, Bio-Red) were treated with DNase-1 (Roche Diagnostics GmbH, Mannheim Germany. 10 U/ml) for 1 h in DNase-1 digestion buffer (PeqLab. Erlangen, Germany). The DNase-1 solution was removed and the indirect immunofluorescence was performed as instructed by the test kit's manual. Slides were then examined by fluorescence microscopy (DMI 40008, Leica). NETs were generated as previously described. The used buffer was then replaced with HBSS buffer containing 2 mM calcium, 4 mM bicarbonate, 2 mM magnesium, 10 mM HEPES and DNase-1 (10 U/ml) for 20 min at room temperature. After this step, ethanol fixation, staining and fluorescence microscopy was performed as described above. Coated microspheres were subjected to DNase-1 in HBSS with 2 mM calcium, 4 mM bicarbonate, 2 mM magnesium, 10 mM HEPES and DNase-1 (10 U/ml) for 20 min at room temperature. Subsequently, immunostaining and flow cytometric ANCA diagnostics were performed as mentioned above.

The invention claimed is:

1. Method for detecting and quantifying anti-neutrophil-cytoplasmic antibodies (ANCA) in a blood plasma or serum sample from a human patient suspected of suffering from an autoimmune disease, comprising the steps of:
   (a) obtaining a predetermined number of human polymorphonuclear neutrophils (PMNs);
   (b) providing an equivalent number of polystyrene or latex microspheres of predetermined optical and physical properties, said microspheres having a diameter from 1 to 10 μm;
   (c) contacting and incubating said predetermined number of human polymorphonuclear neutrophils (PMNs) with said equivalent number of polystyrene or latex microspheres;
   (d) inducing formation of extracellular traps (NETs) by said polymorphonuclear neutrophils (PMNs) having antigens recognized by anti-neutrophil-cytoplasmic antibodies (ANCA) in the absence of chemical(s) capable of stimulating said polymorphonuclear neutrophils;
   (e) allowing interaction of said polystyrene or latex microspheres and said extracellular traps (NETs), so that NET-coated microspheres having antigens recognized by anti-neutrophil-cytoplasmic antibodies (ANCA) are obtained;
   (f) contacting said NET-coated microspheres with said sample of blood plasma or serum; creating conditions for interaction of anti-neutrophil-cytoplasmic antibodies (ANCA) with said antigens on said NET-coated microspheres;
   (g) labeling said anti-neutrophil-cytoplasmic antibodies bound onto said NET-coated microspheres;
   (h) analyzing said NET-coated microspheres with labeled anti-neutrophil-cytoplasmic antibodies by flow cytometric methods, so that the presence of anti-neutrophil-cytoplasmic antibodies (ANCA) in the blood plasma or serum sample can be quantitatively determined.

2. The method according to claim 1, wherein said autoimmune disease is selected from the group consisting of ANCA-associated vasculitides, granulomatosis with polyangiitis, microscopic polyangiitis, eosinophilic granulomatosis with polyangiitis, primary pauci-immune necrotizing and crescentic glomerulonephritis, drug-induced vasculitides, cystic fibrosis, inflammatory bowel disease, primary sclerosing cholangitis, rheumatoid arthritis, systemic lupus erythematosus and psoriasis.

3. The method according to claim 1, wherein said microspheres have a diameter from 1.5 µm to 6 µm.

4. The method of claim 1, further comprising the use of a pipettable composition of microspheres associated with or coupled with one or more ANCA targeting antigens selected from the group consisting of proteinase 3 (PR3), myeloperoxidase (MPO), elastase, cathepsin G, lactoferrin, lysozyme, permeability-increasing protein (BPI) and combinations thereof.

5. The method according to claim 3, wherein said polystyrene or latex microspheres have a diameter from 2 µm to 4 µm.

6. The method according to claim 1, wherein said anti-neutrophil-cytoplasmic antibodies bound onto said NET-coated microspheres are labeled with labeled secondary antibodies, or fragments thereof, which specifically recognize human immunoglobulins.

7. The method according to claim 1, wherein at least one of said antigens recognized by anti-neutrophil-cytoplasmic antibodies is a member of the group consisting of proteinase 3 (PR3), myeloperoxidase (MPO), elastase, cathepsin G, lysozyme, lactoferrin, and bactericidal permeability increasing protein (BPI).

* * * * *